US012667658B2

(12) United States Patent
Werner et al.

(10) Patent No.: US 12,667,658 B2
(45) Date of Patent: Jun. 30, 2026

(54) CASSETTE FOR A CONSOLE OF AN OPHTHALMOSURGICAL SYSTEM, AND OPHTHALMOSURGICAL SYSTEM

(71) Applicant: Carl Zeiss Meditec AG, Jena (DE)

(72) Inventors: Andreas Werner, Aalen (DE); Steffen Kibbel, Lauchheim (DE); Giulio Saltini, San Giovanni in Persiceto (IT); Peter Eichert, Bissingen (DE)

(73) Assignee: Carl Zeiss Meditec AG, Jena (DE)

( * ) Notice: Subject to any disclaimer, the term of this patent is extended or adjusted under 35 U.S.C. 154(b) by 787 days.

(21) Appl. No.: 17/950,059

(22) Filed: Sep. 21, 2022

(65) Prior Publication Data

US 2023/0090690 A1 Mar. 23, 2023

(30) Foreign Application Priority Data

Sep. 21, 2021 (DE) ...................... 10 2021 124 413.7

(51) Int. Cl.
*A61M 3/02* (2006.01)
*A61F 9/007* (2006.01)
(Continued)

(52) U.S. Cl.
CPC ....... *A61M 3/0201* (2021.05); *A61F 9/00736* (2013.01); *A61M 3/0254* (2013.01); (Continued)

(58) Field of Classification Search
CPC ................ A61F 9/0008; A61F 9/00736; A61F 9/00745; A61F 9/00754; A61M 2205/12; (Continued)

(56) References Cited

U.S. PATENT DOCUMENTS 10,639,196 B2 * 5/2020 Kuebler .............. A61M 3/0216
10,722,619 B2 7/2020 Kuebler et al.
(Continued)

FOREIGN PATENT DOCUMENTS

DE 102016201297 B3 3/2017
DE 202016101475 U1 * 6/2017 ........ A61M 39/1055
(Continued)

OTHER PUBLICATIONS

Office Action issued in German Patent Application No. DE 10 2021 124 413.7, dated Jul. 1, 2022 (from which this application claims priority) and English language translation thereof.
(Continued)

*Primary Examiner* — Shefali D Patel
(74) *Attorney, Agent, or Firm* — Ewers IP Law PLLC; Falk Ewers

(57) ABSTRACT

A cassette for a console of an ophthalmosurgical system for treating an eye is provided. The cassette is configured for insertion into a cassette receiving region of the console and has a fluid pump configured to deliver a treatment fluid, a tube for attachment to a handpiece, and a connection unit for a mechanical connection of a cassette-side end of the tube to a cassette housing of the cassette. The connection unit includes an attachment stub arranged on the cassette housing and a plug-in connector arranged on the cassette-side end of the tube. The attachment stub has a first through opening for the treatment fluid. The plug-in connector has a second through opening for the treatment fluid. When the plug-in connector is connected to the attachment stub in a fluid-tight manner, the plug-in connector can be rotated about a longitudinal axis of the first through opening and the second through opening.

5 Claims, 6 Drawing Sheets

(51) Int. Cl.
    *A61M 39/08*         (2006.01)
    *A61M 39/10*         (2006.01)

(52) U.S. Cl.
    CPC ........ *A61M 39/08* (2013.01); *A61M 39/1011*
        (2013.01); *A61F 9/00745* (2013.01); *A61M*
        *2205/12* (2013.01); *A61M 2210/0612*
        (2013.01)

(58) Field of Classification Search
    CPC ........ A61M 2210/0612; A61M 3/0201; A61M
        39/10; A61M 39/1011; A61M 39/1055;
        A61M 39/12; A61M 2039/1061; A61M
        3/0233; A61M 3/0254; A61M 5/14;
        A61M 5/142; A61M 5/50; A61M 39/08;
        A61M 2205/27; A61M 2205/273

See application file for complete search history.

(56) References Cited

U.S. PATENT DOCUMENTS

| | | |
|---|---|---|
| 2006/0157984 A1 | 7/2006 | Rome et al. |
| 2008/0058727 A1 | 3/2008 | Domash et al. |

FOREIGN PATENT DOCUMENTS

| | | |
|---|---|---|
| EP | 2252345 B1 | 9/2016 |
| EP | 3021803 B1 | 12/2017 |
| GB | 2451891 A | 2/2009 |
| WO | 9422520 A1 | 10/1994 |

OTHER PUBLICATIONS

European Search Report dated Feb. 13, 2023, of European counterpart application 22196209.5, and English language translation thereof.

* cited by examiner

CASSETTE FOR A CONSOLE OF AN OPHTHALMOSURGICAL SYSTEM, AND OPHTHALMOSURGICAL SYSTEM

CROSS REFERENCE TO RELATED APPLICATIONS

This application claims priority to German patent application DE 10 2021 124 413.7, filed Sep. 21, 2021, the entire content of which is incorporated herein by reference.

TECHNICAL FIELD

The disclosure relates to a cassette for a console of an ophthalmosurgical system for treating an eye, the cassette being configured for insertion into a cassette receiving region of the console and having at least one fluid pump for delivering a treatment fluid, a tube for attachment to a handpiece of the ophthalmosurgical system, and a connection unit for the mechanical connection, secured against detachment, of a cassette-side end of the tube to a cassette housing of the cassette. The disclosure also relates to an ophthalmosurgical system for treating an eye, having at least one cassette which includes at least one fluid pump for delivering a treatment fluid, a console having a cassette receiving region for receiving the cassette and drive means for driving the fluid pump arranged in the cassette, and an ophthalmosurgical handpiece which is intended for treating a crystalline lens of the eye and is fluidically couplable at least to the cassette.

BACKGROUND

Ophthalmosurgical systems, which have consoles and ophthalmosurgical handpieces couplable thereto, and cassettes for a console of an ophthalmosurgical system for treating an eye are known in the related art, and so in principle there is no need for separate documentary evidence of such systems. The handpiece is generally fluidically coupled to the console, in particular the cassette inserted in the console, via a tube. Various surgical techniques are known for example for the treatment of a clouding of the crystalline lens, also known in medicine as cataract. The most widespread technique is phacoemulsification, in which a thin hollow needle is introduced into a capsular bag, in which the crystalline lens is arranged, and is induced to make ultrasonic vibrations. The lens can be emulsified with the vibrating hollow needle, and lens particles released in the process can be aspirated through an aspiration line with a pump. In the process, an irrigation fluid is supplied. The lens particles are aspirated, together with the fluid, as aspiration fluid. As soon as the lens has been completely emulsified and removed, a new artificial lens can be inserted into the then empty capsular bag. The treated patient can in this way recover good vision.

An advanced ophthalmosurgical system that has proven particularly suitable for phacoemulsification is described in DE 10 2016 201 297 B3, for example. In this system, two fluid pumps fluidically connected in parallel are used in each case for the irrigation and also for the aspiration. Each of the fluid pumps has a pump chamber, and a drive chamber separated from the pump chamber with an elastic partition element. For the operation as intended of the fluid pump, the drive chamber is acted upon by a drive fluid whose drive pressure is varied for performing a respective pump stroke. Depending on this, a deflection position of the elastic partition element thus changes, which has a corresponding effect on the pump chamber. The pump chamber is acted upon by the respective treatment fluid, for example the irrigation fluid, the aspiration fluid or the like. The delivery action can then be achieved by suitably controlling an inlet valve and an outlet valve of the fluid pump.

A deflection position of the elastic partition element is detected with a deflection position sensor assigned to the respective fluid pump. A control device of the ophthalmosurgical system, in particular of the console, controls the function of the fluid pump at least depending on a sensor signal of the deflection position sensor and on a drive pressure signal supplied with a drive pressure sensor. In addition, the control device can, for example, control the inlet valve and the outlet valve.

By alternate actuation of the respective two fluid pumps connected in parallel, a volumetric flow with very little fluctuation can be obtained during a surgical procedure. In this way, an almost constant intraocular pressure can be obtained in the capsular bag. As long as sufficient irrigation fluid can be delivered, the system can also be operated almost without interruption of the flow of irrigation fluid, even during a very protracted surgical procedure.

For the supply of the handpiece, the ophthalmosurgical system generally has at least one tube, which in particular fluidically couples the console to the handpiece, such that the irrigation fluid can be fed to the handpiece and the aspiration fluid can be removed from the handpiece. Generally, at least the elements in contact with the treatment fluid are arranged in the separate cassette, which is exchangeably insertable into a cassette receiving region of the console. Therefore, the console-side attachment of the at least one tube is usually provided on the cassette.

In the related art, the tube is often fixedly connected to the cassette by being connected, for example, to the cassette housing via a welded connection or adhesive bond. This makes it possible to have the effect that the connection of the tube to the cassette can be secured against detachment. As a result of this, an improved sterility of the ophthalmosurgical system can be achieved.

However, this rigid connection has proven to be disadvantageous to the effect that the handling of the handpiece during operation as intended of the ophthalmosurgical system can be made more difficult owing to the in particular inflexible approach to the cassette. Furthermore, it has proven to be disadvantageous that, when the cassette is in storage or being transported, for example in packaging, the tube can become slightly bent, as a result of which its properties can unfavorably change, particularly because the tube is fixedly connected to the cassette.

SUMMARY

It is an object of the disclosure to provide a cassette for use in a console of an ophthalmosurgical system, and to provide such a system with higher operational reliability.

The solution proposed by the disclosure is a cassette for a console of an ophthalmosurgical system for treating an eye, and an ophthalmosurgical system for treating an eye.

Advantageous developments emerge from the features of the dependent claims.

With respect to a cassette of the type in question for a console of an ophthalmosurgical system for treating an eye, the disclosure in particular provides that the connection unit includes an attachment stub, which is arranged on the cassette housing and has a through opening for the treatment fluid, and a plug-in connector, which is on the cassette-side end of the tube and likewise has a through opening for the treatment fluid, with the plug-in connector, when it is connected to the attachment stub, being held in a fluid-tight manner with respect to the attachment stub and so as to be able to rotate about a longitudinal axis of the through opening.

As regards an ophthalmosurgical system of the type in question, the disclosure provides in particular that the cassette is configured according to the disclosure.

The disclosure is based, inter alia, on the idea that a mechanical connection that is secured against detachment and enables rotatability about a longitudinal axis of the through opening makes it possible to improve the flexibility of the tube with respect to the cassette or the console, such that the disadvantages described in the introduction can at least partially be eliminated. Specifically, as a result of the rotatability of the tube with respect to the cassette, it is possible not only to reduce the risk of the tube bending, in particular during intended use of the ophthalmosurgical system and within transportation packaging, but also to achieve improved guidance of the tube during a surgical procedure on the eye. This not only facilitates transport and storage, but also the intended use and results in higher operational reliability.

The connection unit of the disclosure makes it possible to have the effect that the tube is rotatable with respect to the cassette, although it is connected to the cassette in such a way that it is secured against detachment. This makes it possible firstly to obtain a connection as in the related art, which is permanent in particular from a sterility perspective, once the cassette has been connected to the tube during production, and secondly to achieve flexible handling of the tube, by way of which the disadvantages with respect to the intended use and also storage and transport can be reduced. The connection unit is therefore configured to establish a one-time connection that typically cannot be detached again, without damaging or destroying the cassette and/or the tube, in particular the connection unit.

Even if in the present case the intention is for the cassette housing to include the attachment stub and the tube to include the plug-in connector, in the context of a cinematic reversal it is naturally also possible to provide a dual configuration, the plug-in connector being provided on the cassette and the attachment stub on the tube. For a connection of this type, the same considerations apply.

Furthermore, the disclosure makes it possible to use different materials for the tube and the cassette, in particular the cassette housing, irrespective of whether these materials are suitable for mutual adhesive bonding or welding. This makes it possible to individually adapt the selection of materials for the tube and the cassette housing to the respective operational and usage requirements.

Both the attachment stub and the plug-in connector have a respective through opening for the treatment fluid. In the connected state, the treatment fluid can be guided through the through openings. To that end, the through openings are fluidically connected to one another in the connected state.

The through openings of the attachment stub and of the plug-in connector can have substantially the same configuration in terms of an internal cross section. Depending on the configuration, the internal cross section of the through openings may also at least partially differ from one another. However, it is typically the case that a cross-sectional area of the respective internal cross sections of the through openings is substantially the same. This naturally also applies to a contour of an edge of the respective cross-sectional areas.

A suitably correspondingly configured attachment stub and plug-in connector additionally also makes it possible to obtain a substantially fluid-tight connection in the joined-together state. The connection unit is typically configured in such a way that a rotatability can be achieved over an angle of rotation of at least approximately 120°. The angle of rotation is typically approximately 0° to approximately 240°. Particularly advantageously, an unlimited rotational movement with respect to the angle is enabled.

The plug-in connector has a plug-in opening for the attachment stub and the attachment stub has a plug-in projection for plugging into the plug-in opening, with the respective through openings leading into the plug-in opening or the plug-in projection, respectively, with the result that the through openings are in line with one another, with the plug-in connector having at least one latching element which is configured to latch to a corresponding latching element of the attachment stub. This makes it possible to easily provide the connection unit, in that the plug-in connector is connected to the attachment stub. The respective latching elements latch into one another such that a mechanically fixed connection can be obtained, at least in an axial direction. By suitably configuring the latching elements, the rotatability can be achieved. In the process, it can be provided that the latching elements at least partially are not accessible from the outside, with the result that unlatching without damaging the connection unit is largely prevented. To that end, the latching elements may be arranged in a region of the plug-in opening and of the plug-in projection. After the connection, it can be ensured in this way that the connection unit no longer can be brought into the detached state non-destructively.

Furthermore, it is provided that the latching element of the attachment stub is at least in the form of a latching lug, which can be latched into a typically encircling latching receptacle of the plug-in connector. However, not just a single latching lug has to be provided on the attachment stub. Depending on requirements, it is also possible to form a plurality of latching lugs, which can be arranged for example distributed over a circumference of the attachment stub. The latching lugs may at least partially also be axially offset with respect to one another. The latching receptacle of the plug-in connector may for example be formed by a groove or by recesses. It is typically an encircling groove, so that unlimited rotatability of the tube with respect to the cassette housing or the cassette can be achieved. The latching receptacle is typically arranged on the inside of the latching opening of the plug-in connector, with the result that it is substantially not accessible from the outside.

It is also provided that the connection unit has a sealing element. The fluidic seal can be improved in the region of the connection unit with the sealing element. In particular, the sealing element may be adapted to the treatment fluid such that, in addition to good sealing, in particular chemical interaction with the treatment fluid can be largely avoided. To that end, a material of the sealing element may be selected accordingly. Furthermore, the sealing element also makes it possible to further improve the sterility, because the penetration of germs from outside the connection unit can be further reduced. The sealing element may be in the form, for example, of a O ring, a sealing disk, combinations thereof or the like. In principle, it is naturally also possible to provide multiple different sealing elements which together provide or improve the sealing of the connection unit. A further advantage of the sealing element is that aging-related creep or deformation of the materials of the connection unit can be compensated and thus a sealed connection can be achieved over the entire service life of the product.

It is also provided that a portion, adjoining the plug-in connector, of the tube is angled away with respect to the longitudinal axis and in particular forms an angle of approximately 90° with the longitudinal axis. This makes it possible to have the effect that, together with the rotatability, a particularly favorable positioning of the tube with respect to the cassette housing and thus overall, with respect to the cassette or the console can be improved.

The advantages and effects indicated for the cassette according to the disclosure are of course also equally applicable to the ophthalmosurgical system equipped with the cassette according to the disclosure, and vice versa.

Further features of the disclosure are evident from the figures and the description of the figures. The features and combinations of features mentioned in the description above and the features and combinations of features mentioned in the description of the figures below and/or shown only in the figures can be used not only in the respectively specified combination but also in other combinations, without departing from the scope of the disclosure. Consequently, exemplary embodiments of the disclosure which are not explicitly shown and explained in the figures but emerge from and can be created by separate combinations of features from the explained embodiments should also be considered to be included and disclosed.

BRIEF DESCRIPTION OF THE DRAWINGS

The disclosure will now be described with reference to the drawings wherein.

DESCRIPTION OF EXEMPLARY EMBODIMENTS

Figure 1:
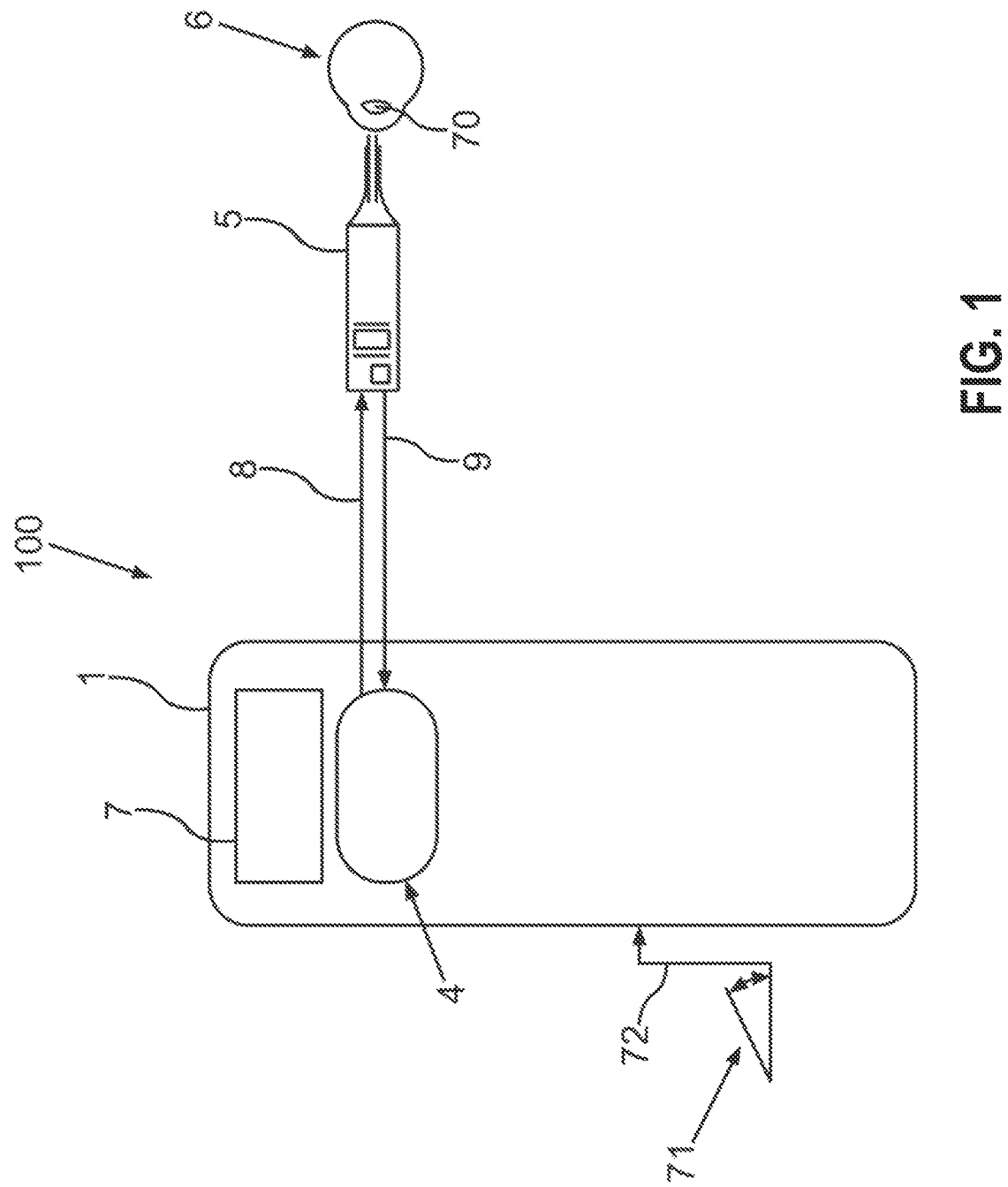
FIG. 1 shows a schematic block diagram of an ophthalmosurgical system, with a console and with a handpiece, which is coupled with a tube to the cassette inserted in the console according to an exemplary embodiment of the disclosure.

FIG. 1 shows, in a schematic block diagram, an ophthalmosurgical system 100, which serves for treating an eye 6. The ophthalmosurgical system 100 has a surgical instrument 5 as handpiece. The ophthalmosurgical system 100 also has a console 1 for connecting and operating the handpiece 5 during operation as intended. Furthermore, the ophthalmosurgical system 100 has a foot-operated control unit 71, which in the present case is in the form of a foot pedal. The foot-operated control unit 71 is wirelessly couplable to the console 1. The console 1 also has a control unit 7 and also fluidic supply units, which serve inter alia for feeding an irrigation fluid 3 to the handpiece 5 by way of an irrigation fluid flow path 8 and removing an aspiration fluid from the handpiece 5 by way of an aspiration fluid flow path 9. In the present case, the irrigation fluid flow path 8 and the aspiration fluid flow path 9 are each provided by a tube 61.

The foot-operated control unit 71 in the present case is of a cableless configuration, for which reason it is supplied with electrical energy from an electrical energy store, not illustrated in more detail, at least during operation as intended. In addition, the foot-operated control unit 71, during operation as intended, communicates with the control unit 7 via a wireless communication link 72, such that an operating state of the handpiece 5 can be at least partially set.

Figure 2:
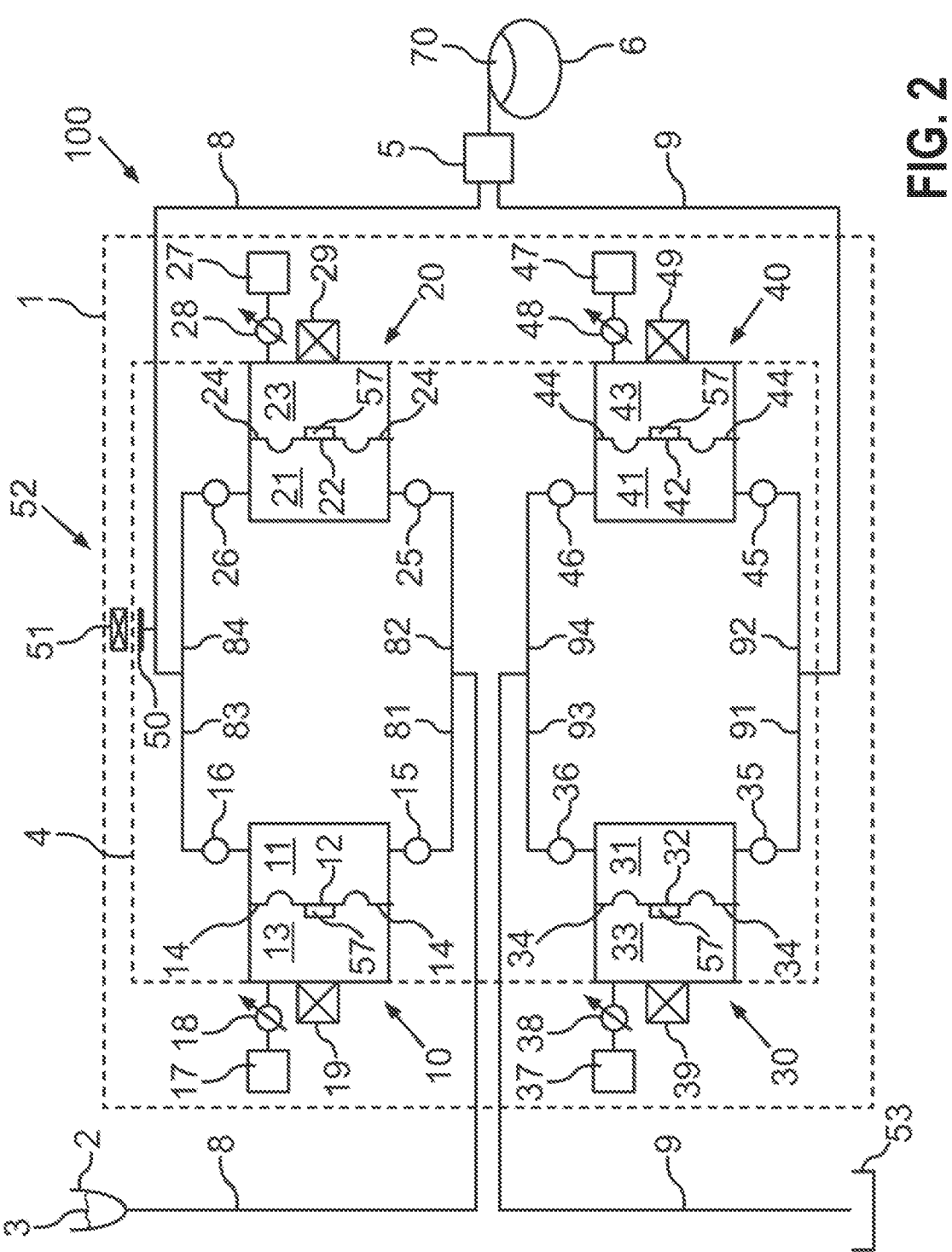
FIG. 2 shows a schematic block diagram of the ophthalmosurgical system according to a first exemplary embodiment of the disclosure.
Figure 3:
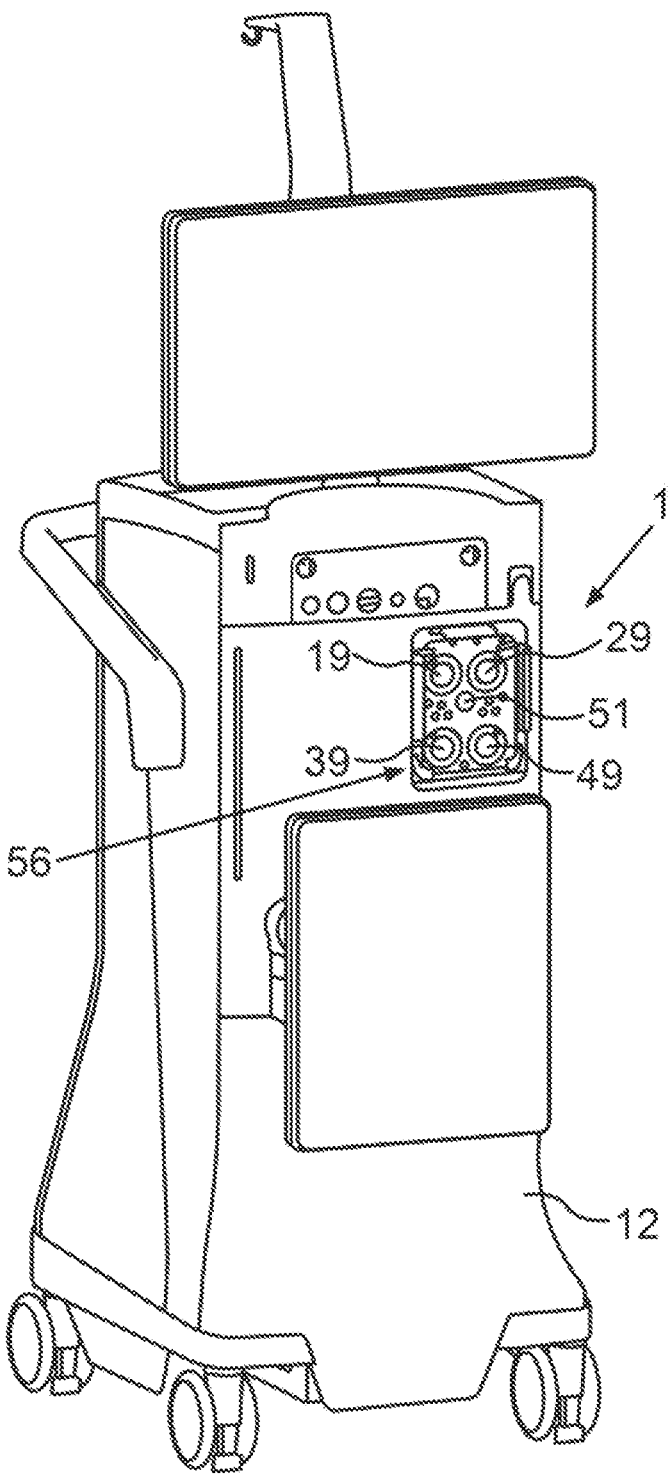
FIG. 3 shows a schematic perspective illustration of a console of the system according to FIG. 2.
Figure 4:
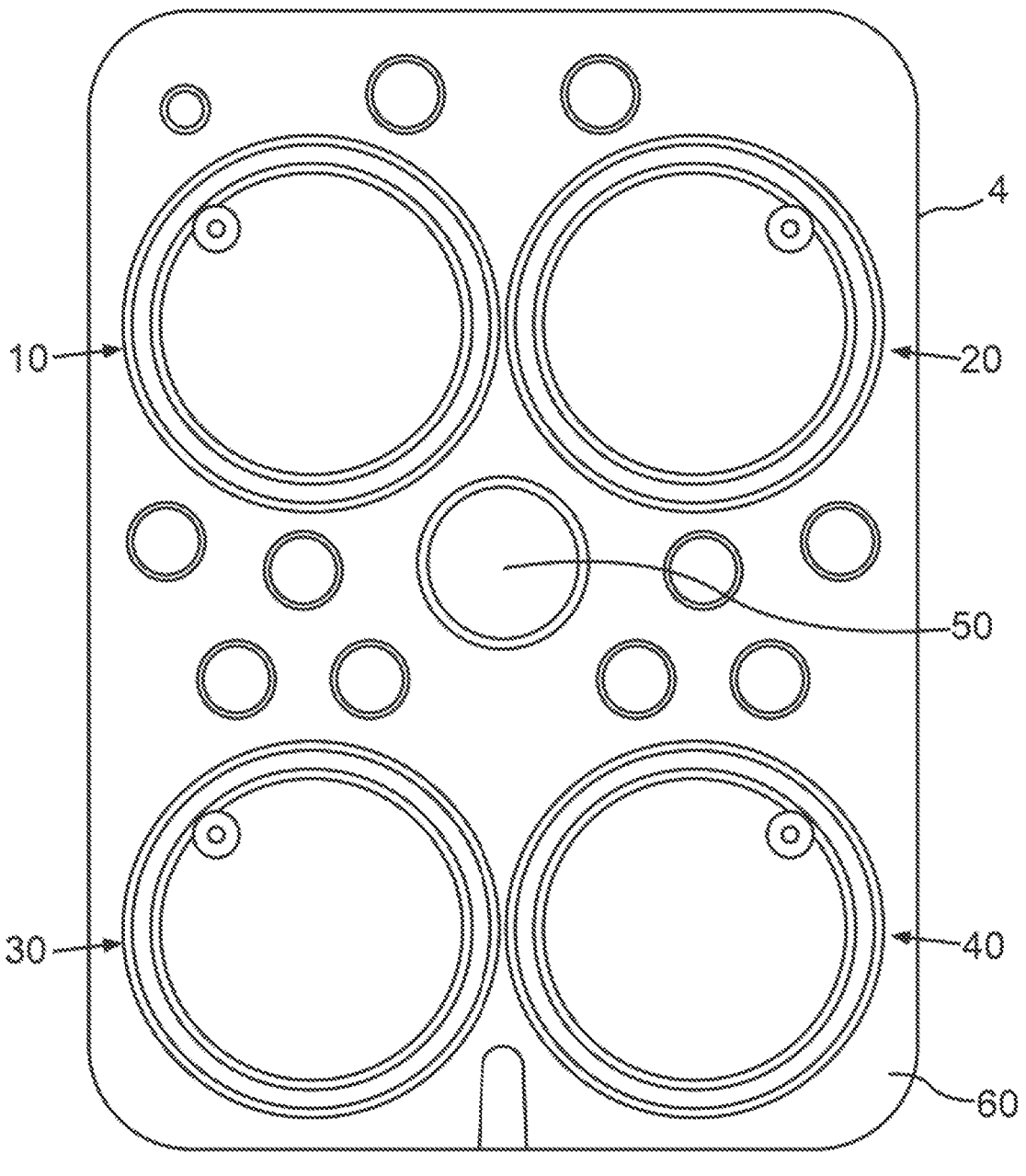
FIG. 4 shows a schematic plan view of an attachment side of a cassette for the system according to FIG. 2.

FIG. 2 shows a schematic block diagram of the ophthalmosurgical system 100 according to FIG. 1. The system 100 has the console 1, to which an irrigation fluid container 2 containing an irrigation fluid 3 is coupled. In addition, the system 100 has a cassette 4 which is insertable into the cassette receiving region 56 of the console 1 (cf. FIG. 3). In addition to delivering the irrigation fluid 3 to the handpiece 5, which serves for phacoemulsification of a lens 70 of an eye 6, the cassette 4 also serves to remove an aspiration fluid, that arises in the process, from a treatment region of the eye 6. In the present case, the handpiece 5 serves for phacoemulsification of the lens 70 of the eye 6. FIG. 3 shows a schematic perspective illustration of the console 1 without the cassette 4. FIG. 4 shows a schematic plan view of an attachment side of the cassette 4 for connection to the console 1 in the cassette receiving region 56.

The system 100 further has an irrigation fluid flow path 8, which runs from the irrigation fluid container 2 to the handpiece 5 via the cassette 4. In addition, the system 100 has a first fluid pump 10 with a first pump chamber 11, and a first drive chamber 13 separated therefrom by a first partition element 12. The first partition element 12 is typically deformable. The first partition element 12 has an edge 14, with which it is connected to the fluid pump 10. At its edge 14, the partition element 12 is not displaceable in an axial direction that runs parallel to a partition element center axis. The partition element 12 is typically securely clamped at its edge 14.

The irrigation fluid 3 can be delivered to the first pump chamber 11 via the irrigation fluid flow path 8 and a first inlet valve 15 of the first pump chamber 11, depending on a valve state of the inlet valve 15. Moreover, it can be removed from the pump chamber 11 again via an outlet valve 16, depending on the valve state of the latter. The first drive chamber 13 can be acted upon by a first drive fluid 17, which can be delivered with a proportional valve 18 arranged in the console 1. Depending on a differential pressure between the first drive fluid 17 in the first drive chamber 13 and the irrigation fluid as treatment fluid in the first pump chamber 11, there is an elastic deformation, or deflection or displacement, of the first partition element 12. An absolute value of the pressure in the first drive chamber 13 is greater than a magnitude of the pressure in the first pump chamber 11. When the inlet valve 15 is closed and the outlet valve 16 is opened, the irrigation fluid can flow out of the first pump chamber 11 into a subsidiary path 83 attached to the outlet valve.

A deflection position of the first partition element 12 can be detected with a first deflection position sensor 19, which is arranged outside the first fluid pump 10, for example in the console 1. In the present case, the first deflection position sensor 19 is in the form of a sensor unit in the style of an inductive position encoder. The function of the deflection position sensor 19 will be explained in more detail below.

As is evident from FIG. 1, the drive chamber 13 and the pump chamber 11 with the partition element 12 are arranged in the cassette 4. By arranging the cassette 4 in the console 1, the fluid pump 10 is coupled to a drive fluid feed of the console 1 and to the deflection position sensor 19 arranged in the console 1, and so it is possible to obtain the desired pump function and the detection function for detecting the deflection position of the first elastic partition element 12.

It is also evident from FIG. 2 that a second fluid pump 20 is fluidically connected in parallel to the first fluid pump 10. In the present case, the second fluid pump 20 is configured like the fluid pump 10. Therefore, the irrigation fluid flow path 8 in the cassette 4 is divided into a first subsidiary path 81 and a second subsidiary path 82. The first subsidiary path 81 is attached to the first inlet valve 15, and the second subsidiary path 82 is attached to a second inlet valve 25 of the second fluid pump 20.

The second fluid pump 20 has a second pump chamber 21, and a second drive chamber 23 separated from the latter with a second partition element 22. The partition element 22 has a second edge 24, which for example is mounted fixedly in the second fluid pump 20. The second drive chamber 23 can be acted upon by a second drive fluid 27 via a second proportional valve 28 arranged in the console 1. A deflection position of the partition element 22 can be detected with a second deflection position sensor 29, which in the present case has a corresponding configuration to the first deflection position sensor 19. By way of a second outlet valve 26, the irrigation fluid 3 can again leave the second pump chamber 21 into the subsidiary path 84. By way of the subsidiary paths 83, 84, which are attached to the first and the second outlet valve 16, 26 respectively, the irrigation fluid leaving the respective fluid pump 10, 20 can be delivered again to the irrigation fluid flow path 8, in order to be delivered to the instrument 5.

In a region of the fluidic connection of the subsidiary path 83 to the subsidiary path 84, that is to say for example in the downstream irrigation fluid flow path 8, an elastic membrane 50 is formed which is able to contact the irrigation fluid. The membrane 50 is arranged at the cassette 4. The membrane 50 is contacted by a force sensor 51, which for its part is arranged in the console 1 when the cassette 4 is arranged in the cassette receiving region 56 (FIG. 4). The membrane 50, in conjunction with the force sensor 51, forms a detection sensor 52.

During the comminution of the crystalline lens 70, small lens particles are released and can be aspirated together with the delivered irrigation fluid. The irrigation fluid, contaminated with lens particles, is then referred to as aspiration fluid and is conveyed via an aspiration fluid flow path 9 to an aspiration fluid collection container 53. For this purpose, in the present case two further fluid pumps 30, 40 connected in parallel are provided which, in principle, are comparable to the fluid pumps 10, 20 for the irrigation fluid. For this purpose, provision is made inside the cassette 4 that the aspiration flow path 9 likewise divides into two subsidiary paths 91, 92, which are attached via respective inlet valves 35, 45 to the respective fluid pumps 30, 40, specifically here to the respective pump chambers 31, 41. It is also the case here that the pump chambers 31, 41 are separated from respective drive chambers 33, 43 by respective partition elements 32, 42. The partition elements 32, 42 have respective edges 34, 44, which are mounted fixedly in the respective fluid pump 30, 40. By way of respective outlet valves 36, 46 and the subsidiary paths 93, 94 attached thereto, the aspiration fluid can then be removed via the aspiration fluid flow path 9. A third drive fluid 37 can be guided to the third drive chamber 33 with a third proportional valve 38. Correspondingly, a fourth drive fluid 47 can be guided to a fourth drive chamber 43 with a fourth proportional valve 48. The proportional valves 38, 48 are arranged in the console 1. The deflection positions of the partition elements 32, 42 can be detected with respective deflection position sensors 39, 49. In the present case, the two fluid pumps 30, 40 are likewise operated alternately like the fluid pumps 10, 20.

FIG. 3 shows a schematic perspective illustration of the console 1 of the ophthalmosurgical system 100 according to FIG. 1, the illustration including a front side of the console 1. It is evident from FIG. 3 that the console 1 has the cassette receiving region 56, which serves for the detachable arrangement of the cassette 4. The cassette 1 also has a drive fluid supply system, not illustrated, which serves to provide the respective drive fluid for the respective drive chambers 13, 23, 33, 43, the drive fluid being formed by air in the present case. The drive fluid supply system has respective drive fluid sources 17, 27, 37, 47 (FIG. 1) for each of the fluid pumps 10, 20, 30, 40, said drive fluid sources being connected to respective proportional valves 18, 28, 38, 48. The respective drive fluid can be made to act on the respective drive chamber 13, 23, 33, 43 by way of the proportional valves 18, 28, 38, 48 during operation as intended. The console 4 has a console housing 12, in which the elements or units of the console 4 are arranged. The console housing 12 provides the cassette receiving region 56, in which the cassette 4 can be arranged.

It is further evident from FIG. 2 that each of the elastic partition elements 12, 22, 32, 42 has a plate element 57 which is also moved when the elastic partition element 12, 22, 32, 42 is moved. In the present case, the plate element 57 is in the form of a metal plate and made from a ferromagnetic material. The plate element 57 has a thickness which is smaller than a thickness of the elastic partition element 12, 22, 32, 42.

The console 1 also has a respective deflection position sensor 19, 29, 39, 49 for each of the fluid pumps 10, 20, 30, 40, in the present case the deflection position sensor providing a respective sensor unit which utilizes a magnetic field in order to detect the position of the respective plate element 57 and hence the position of the respective elastic partition element 12, 22, 32, 42.

Figure 5:
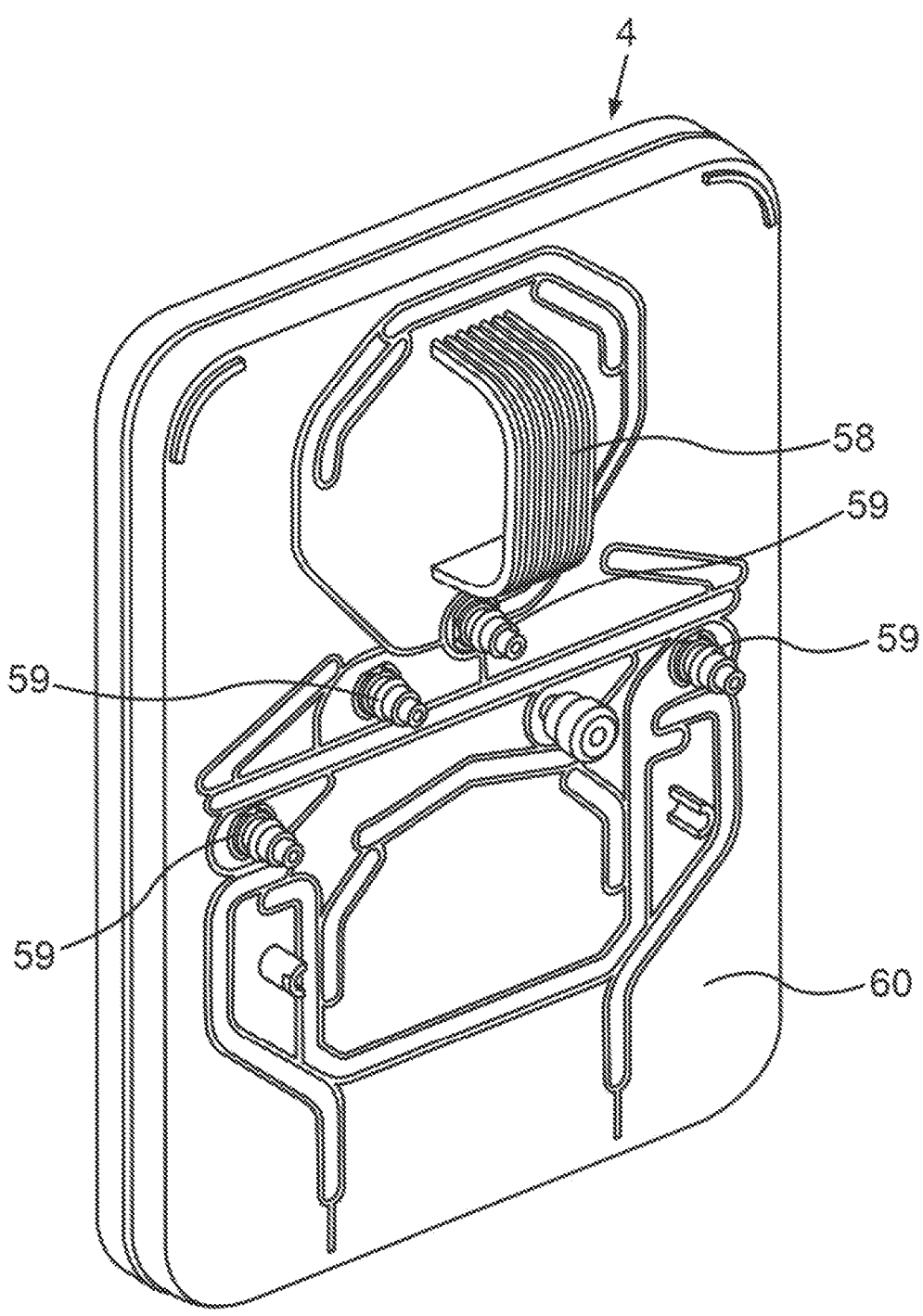
FIG. 5 shows a schematically perspective view of the cassette according to FIG. 4 on an operator side, which is opposite the attachment side.

FIG. 4 shows a schematic plan view of the cassette 4 with an attachment side, which faces the console 1 in the state arranged in the cassette receiving region 56. The cassette 4 has a cassette housing 60. FIG. 5 shows, in a perspective view of the cassette 4, an operator side, which is opposite the attachment side. It can be seen that, in a top region, the cassette 4 has a handle 58, with which the cassette 4 can be manually inserted into and removed from the cassette receiving region 56. Furthermore, on the operator side, there are provided attachment stubs 59 which, as will be explained in more detail below, are each mechanically connected to a tube 61, specifically in such a way that the connection provided as a result is secured against detachment. To that end, a connection unit 62 (FIG. 6) is provided. In FIG. 5, only the attachment stubs 59 of the connection unit 62 without the tube 61 are visible, that is to say prior to connection of the cassette housing 60 to the respective tube 61.

Figure 6:
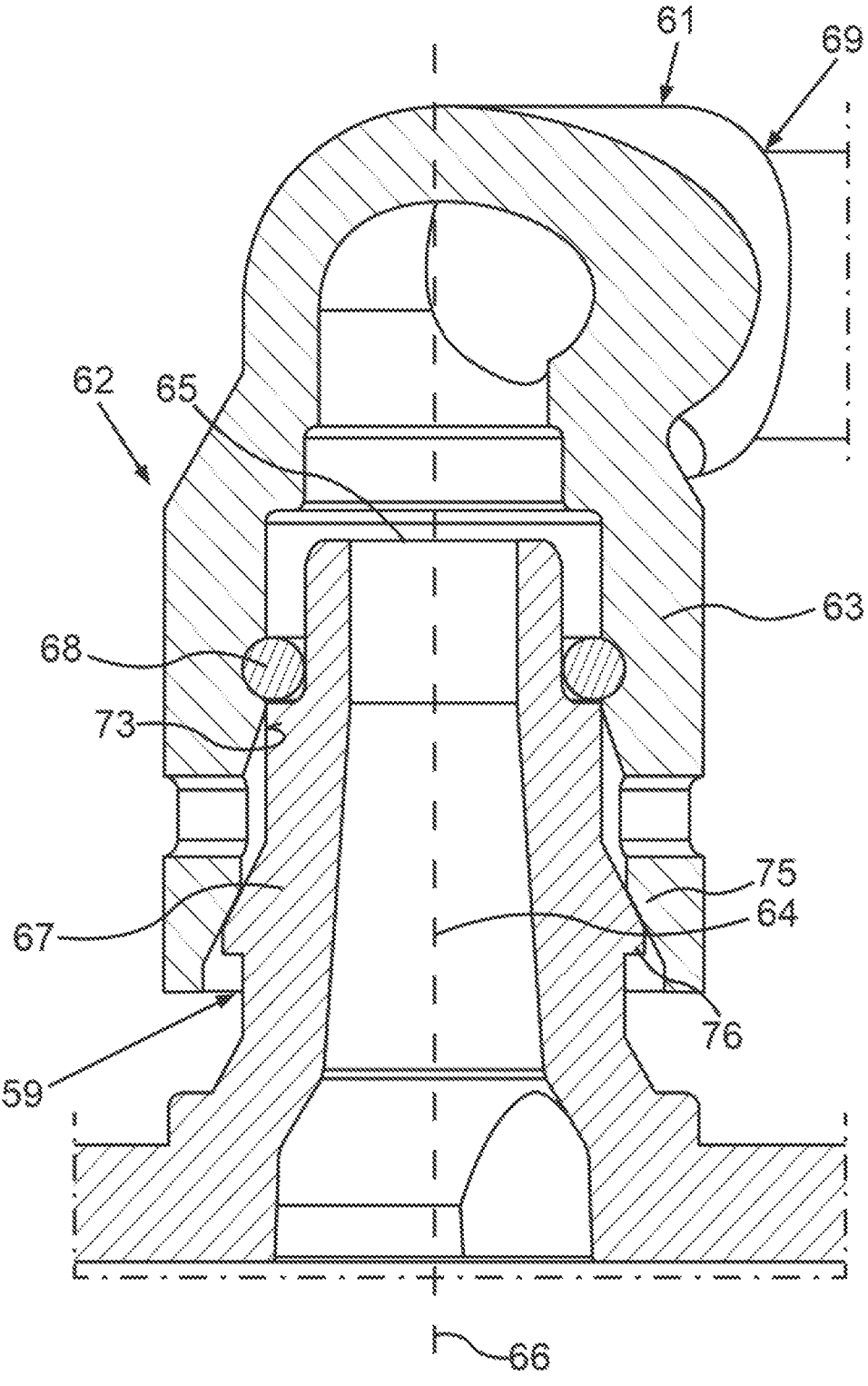
FIG. 6 shows a schematic sectional illustration of a detail of the cassette according to FIG. 5 in the region of a connection to a tube for one of the treatment fluids.

FIG. 6 shows a schematic sectional view in the region of one of the connection units 62 of the cassette 4. The connection unit 62 includes the attachment stub 59, which is arranged on the cassette housing 60 and has a through opening 64 for the treatment fluid. The connection unit 62 also has a plug-in connector 63, which is on the cassette-side end of the tube 61 and likewise has a through opening 65 for the treatment fluid. The plug-in connector 63, when it is connected to the attachment stub 59, is held in a fluid-tight manner with respect to the attachment stub 59 and so as to be able to rotate about a longitudinal axis 66 of the through openings 64, 65, as illustrated in the schematic sectional view according to FIG. 6.

The plug-in connector 63 has a plug-in opening 73 for the attachment stub 59 and the attachment stub 59 has a plug-in projection 67 for plugging into the plug-in opening 73. The respective through openings 64, 65 lead into the plug-in opening 73 or the plug-in projection 67, respectively, with the result that the through openings 64, 65 are in line with one another in the connected state. The plug-in connector 63 has a latching element 75, not illustrated, which is configured to latch to a corresponding latching element 76 of the attachment stub 59. In the present case, the corresponding latching element of the attachment stub 59 is formed by multiple latching lugs, which are latchable into an encircling groove of the plug-in connector 63, which groove provides a latching receptacle as latching element of the plug-in connector 63. The latching lugs and the groove are arranged in a connection region of the connection unit 62 such that they are not accessible for the purpose of detaching the latching connection. This secures the connection unit 62 against detachment.

It can also be seen that the connection unit 62 has a sealing element 68, which is arranged between an end-face recess in the attachment stub 59 and an inner side of the plug-in opening 73. In the present case, the sealing element 68 is configured in the manner of an O ring. In the present case, it has an elastic form, with the result that good sealing can be achieved despite the rotatability.

A portion 69, adjoining the plug-in connector 63, of the tube 61 is angled away with respect to the longitudinal axis 66 and forms an angle of approximately 90° with the longitudinal axis 66. This makes it possible to achieve readily adjustable tube guidance for the tube 61. In the present case, it is provided that the connection unit 62 illustrated here is provided correspondingly for all four attachments of the cassette 4. By way of the tubes 61, the irrigation fluid 3 can be fed to the cassette 4 as well as from the reservoir 2, with the result that it can be fed to the handpiece 5 via a further one of the attachments. Correspondingly, the aspiration fluid can be fed from the handpiece 5 to the cassette 4 via a tube 61 and be fed to an aspiration fluid collection container 53 for the aspiration fluid via a further attachment stub 59 of the cassette 4.

During the production of the cassette 4, the connection unit 62 is completed, with the respective plug-in connector 63 of the tubes 61 being plugged and latched onto the respective attachment stubs 59 for the purpose of forming the respective connection units 62 in one of the last production steps.

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Console
2 Irrigation fluid container
3 Irrigation fluid
4 Cassette
5 Handpiece, surgical instrument
6 Eye
7 Control unit 8 Irrigation fluid flow path
9 Aspiration flow path
10 First fluid pump
11 First pump chamber
12 First partition element
13 First drive chamber
14 Edge
15 First inlet valve
16 First outlet valve
17 First drive fluid
18 First proportional valve
19 Deflection position sensor
20 Second fluid pump
21 Second pump chamber
22 Second partition element
23 Second drive chamber
24 Edge
25 Second inlet valve
26 Second outlet valve
27 Second drive fluid
28 Second proportional valve
29 Deflection position sensor
30 Third fluid pump
31 Third pump chamber
32 Third partition element
33 Third drive chamber
34 Edge
35 Inlet valve
36 Outlet valve
37 Third drive fluid
38 Proportional valve
39 Deflection position sensor
41 Fourth pump chamber
42 Fourth partition element
43 Fourth drive chamber
44 Edge
45 Fourth inlet valve
46 Fourth outlet valve
47 Fourth drive fluid
48 Fourth proportional valve
49 Deflection position sensor
50 Membrane
51 Force sensor
52 Detection sensor
53 Aspiration fluid collection container
54 Adjustment mechanism
55 Coupling
56 Cassette receiving region
57 Plate element
58 Handle
59 Attachment stub
60 Cassette housing
61 Tube
62 Connection unit
63 Plug-in connector
64 Through opening
65 Through opening
66 Longitudinal axis
67 Plug-in projection
68 Sealing element
69 Portion
70 Lens
71 Foot-operated control unit
72 Communications link
73 Plug-in opening
75 Latching element

76 Corresponding latching element
81, 82, 83, 84, 91, 92, 93, 94 Subsidiary path
100 Ophthalmosurgical system

What is claimed is:

1. A cassette for a console of an ophthalmosurgical system for treating an eye, the cassette being configured for insertion into a cassette receiving region of the console, the cassette comprising:

at least one fluid pump configured to deliver a treatment fluid;

a tube configured to attach an ophthalmosurgical handpiece of the ophthalmosurgical system; and a connection unit for a mechanical connection, secured against detachment, of a cassette-side end of the tube to a cassette housing of the cassette, wherein the connection unit includes an attachment stub arranged on the cassette housing and a plug-in connector arranged on the cassette-side end of the tube, wherein the attachment stub has a first through opening for the treatment fluid, wherein the plug-in connector has a second through opening for the treatment fluid, wherein when the plug-in connector is connected to the attachment stub, the plug-in connector is held in a fluid-tight manner with respect to the attachment stub and can rotate about a longitudinal axis defined by the first through opening and the second through opening, wherein the plug-in connector has a plug-in opening for the attachment stub and the attachment stub has a plug-in projection for plugging the attachment stub into the plug-in opening, wherein the first through opening and the second through opening lead into the plug-in opening or the plug-in projection, respectively, such that the first through opening and the second through opening are in line with one another, wherein the plug-in connector has at least one latching element configured to latch to at least one corresponding latching element of the attachment stub, and wherein the at least one latching element is arranged in a region of the plug-in opening of the plug-in connector which is at least partially not accessible in an attached state of the connection unit such that the connection unit cannot be brought into a detached state non-destructively.

2. The cassette as claimed in claim 1, wherein the at least one corresponding latching element of the attachment stub is a form of a latching lug, which can be latched into a circumferential latching receptacle of the plug-in connector.

3. The cassette as claimed in claim 1, wherein the connection unit has a sealing element.

4. The cassette as claimed in claim 1, wherein a portion, adjoining the plug-in connector, of the tube is angled away with respect to the longitudinal axis and forms an angle of 90° with the longitudinal axis.

5. An ophthalmosurgical system for treating an eye, the ophthalmosurgical system comprising:

the cassette as claimed in claim 1;

a console including a cassette receiving region for receiving the cassette and drive means for driving the at least one fluid pump arranged in the cassette; and an ophthalmosurgical handpiece for treating a crystalline lens of the eye, wherein the ophthalmosurgical handpiece is fluidically couplable to the cassette.

* * * * *